United States Patent
Chen et al.

(10) Patent No.: US 10,442,800 B2
(45) Date of Patent: Oct. 15, 2019

(54) CRYSTAL FORMS OF NBI-98854, PREPARATION METHOD AND USE THEREOF

(71) Applicant: Crystal Pharmaceutical (Suzhou) Co., Ltd., Suzhou, Jiangsu (CN)

(72) Inventors: Minhua Chen, Suzhou (CN); Yanfeng Zhang, Suzhou (CN); Po Zou, Suzhou (CN); Kai Liu, Suzhou (CN); Jinqiu Wang, Suzhou (CN); Xiaoyu Zhang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/311,754

(22) PCT Filed: Jun. 29, 2017

(86) PCT No.: PCT/CN2017/090926
§ 371 (c)(1),
(2) Date: Dec. 20, 2018

(87) PCT Pub. No.: WO2018/001335
PCT Pub. Date: Jan. 4, 2018

(65) Prior Publication Data
US 2019/0218209 A1    Jul. 18, 2019

(30) Foreign Application Priority Data
Jun. 29, 2016   (CN) .......................... 2016 1 0488976

(51) Int. Cl.
*C07D 455/06* (2006.01)
*A61P 25/14* (2006.01)
*A61K 31/473* (2006.01)

(52) U.S. Cl.
CPC .......... *C07D 455/06* (2013.01); *A61K 31/473* (2013.01); *A61P 25/14* (2018.01); *C07B 2200/13* (2013.01)

(58) Field of Classification Search
CPC .............................. C07D 455/06; A61P 25/14
USPC ....................................................... 546/94
See application file for complete search history.

(56) References Cited

FOREIGN PATENT DOCUMENTS

| CN | 101553487 | * | 10/2009 |
| CN | 101553487 A | | 10/2009 |
| WO | 2015/120110 A2 | | 8/2015 |
| WO | 2015/120317 A1 | | 8/2015 |
| WO | 2015/171802 A1 | | 11/2015 |
| WO | 2018/067945 A1 | | 4/2018 |
| WO | 2018/130345 A1 | | 7/2018 |
| WO | 2018/178233 A1 | | 10/2018 |

OTHER PUBLICATIONS

Anonymous, A crystalline form of L-valine (2R, 3R, 11bR)-1,3,4,6,7,11b-hexahydro-9,10-dimethoxy-3-(2-methylpropyl)-2H-benzo[a]quinolizin-2-yl ester. ip.com, XP013172928 4 pages, Sep. 28, 2016.

Anonymous, Novel preparation of crystalline forms L1 and L2 of L-Valine, (2R,3R,11bR)-1,3,4,6,7,11b-hexahydro-9, 10-dimehoxy-3-(2-methylpropyl)-2H-benzo[a]quinolizin-2-yl ester. ip.com, XP002790808 4 pages, Jun. 20, 2017.

Caira, Crystalline Polymorphism of Organic Compounds. Topics in Current Chemistry. 1998;198:163-208.

* cited by examiner

*Primary Examiner* — Niloofar Rahmani
(74) *Attorney, Agent, or Firm* — McCarter & English, LLP; Steven G. Davis; Wei Song

(57) ABSTRACT

The present disclosure relates to novel crystalline forms of NBI-98854 (as shown in formula I), preparation process and use thereof. The crystalline forms of NBI-98854 provided by the present disclosure, named as Form CS1 and Form CS2, can be used for preparing drug product treating tardive dyskinesia. The crystalline forms of NBI-98854 provided by the present disclosure have pharmaceutically acceptable solubility and hygroscopicity, good stability and are stable during storage, thereby avoiding changes in drug solubility, dissolution rate, bioavailability and efficacy due to polymorph transformation. This provides a new and better choice for the preparation of drug product containing NBI-98854, which has significant value for future drug development.

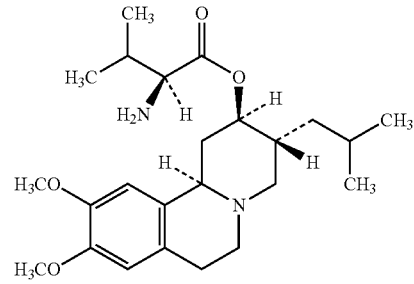

Formula I

14 Claims, 9 Drawing Sheets

CRYSTAL FORMS OF NBI-98854, PREPARATION METHOD AND USE THEREOF

CROSS-REFERENCE TO RELATED APPLICATIONS

The present application is a U.S. national stage application, filed under 35 U.S.C. § 371(c), of International Application No. PCT/CN2017/090926, filed on Jun. 29, 2017, which claims the priority of Chinese Application No. 201610488976.7, filed on Jun. 29, 2016. The entire contents of the aforementioned applications are incorporated herein by reference.

TECHNICAL FIELD

The present disclosure relates to the field of pharmaceutical crystal technology, particularly relates to novel crystalline forms of NBI-98854, and processes for preparation and use thereof.

BACKGROUND

Valbenazine (NBI-98854) developed by Neurocrine, is a novel, highly-selective VMAT2 inhibitor that modulates dopamine release during nerve communication, while at the same time having minimal impact on the other monoamines, thereby reducing the likelihood of "off-target" side effects. NBI-98854 is designed to provide low, sustained, plasma and brain concentrations of active drug to minimize side effects associated with excessive monoamine depletion. NBI-98854 has been approved by FDA on Apr. 11, 2017 for the treatment of tardive dyskinesia. The chemical name of NBI-98854 is (S)-2-amino-3-methyl-butyric acid (2R,3R,11bR)-3-isobutyl-9,10-dimethoxy-1,3,4 6,7,11b-hexahydro-2H-pyrido[2,1-a]isoquinolin-2-yl ester, and the structure is shown as Formula I:

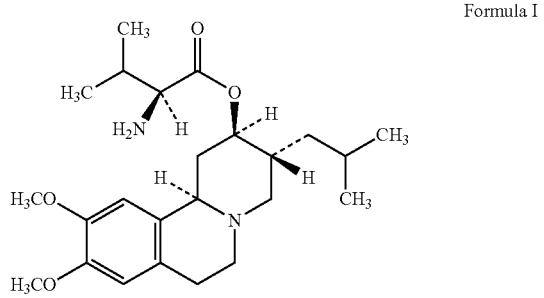 [SMILES: COc1cc2c(cc1OC)[C@H]1C[C@@H](OC(=O)[C@@H](N)C(C)C)[C@H](CC(C)C)CN1CC2]

Formula I

Polymorph or polymorphism is a particular property of certain molecule and molecular composition. Different crystalline forms of certain compounds arise from different molecular packing in the crystal lattice, and these crystalline forms have different crystal structures and physical properties, such as solubility, stability, thermal property, mechanical property, purification capability, X-ray diffraction pattern, infrared absorption spectroscopy, Raman spectroscopy, solid state nuclear magnetic resonance, etc. One or more analytical techniques can be used to distinguish different crystalline forms of the same molecule or molecular composition.

Novel crystalline forms (including anhydrates, hydrates and solvates) of the active pharmaceutical ingredients may offer better processing and physicochemical properties, such as bioavailability, stability, processability, and purification ability. Some novel crystalline forms may serve as intermediate crystal forms to facilitate solid state transformation to desired forms. Novel polymorphs of raw materials provide more solid forms in the formulation, and this can improve dissolution, improve shelf life, and make it easier to process.

Different crystalline forms of solid chemical drugs, with different solubility and stability, can affect the absorption and bioavailability of drugs, and lead to differences in clinical efficacy. The patent CN101553487B disclosed the molecular structure of NBI-98854, but didn't mention the solid or crystalline form of this compound. Moreover, no crystalline form of NBI-98854 was disclosed in prior arts. Therefore, it is quite necessary to study the crystalline form of NBI-98854.

The inventors of the present disclosure discovered two crystalline forms of NBI-98854 during the researches. Moreover, the crystalline forms of NBI-98854 provided by the present disclosure have pharmaceutically acceptable solubility and hygroscopicity, good stability and are stable during storage, thereby avoiding changes in drug solubility, dissolution rate, bioavailability and efficacy due to polymorph transformation. Furthermore, the preparation processes of the crystalline forms CS1 and CS2 provided by the present disclosure are simple and reproducible. The crystallinity of the obtained crystal form is good. The morphologies of crystalline Form CS1 and Form CS2 are needle and block, respectively. Both forms disperse well and have little agglomeration, which are suitable for the development of drug product.

SUMMARY

In order to overcome the disadvantages of prior arts, the main objective of the present disclosure is to provide novel crystalline forms of NBI-98854, processes for preparation and use thereof.

According to the objective of the present disclosure, crystalline form CS1 of NBI-98854 is provided (hereinafter referred to as Form CS1).

Using CuKα radiation, the X-ray powder diffraction pattern of Form CS1 shows characteristic peaks at 2theta values of 9.9°±0.2°, 18.1°±0.2° and 20.3°±0.2°.

Furthermore, the X-ray powder diffraction pattern of Form CS1 shows 1 or 2 or 3 diffraction peaks at 2theta values of 6.0°±0.2°, 6.7°±0.2° and 14.2°±0.2°. Preferably, the X-ray powder diffraction pattern of Form CS1 shows diffraction peaks at 2theta values of 6.0°±0.2°, 6.7°±0.2° and 14.2°±0.2°.

Furthermore, the X-ray powder diffraction pattern of Form CS1 shows 1 or 2 or 3 diffraction peaks at 2theta values of 16.8°±0.2°, 17.5°±0.2° and 22.2°±0.2°. Preferably, the X-ray powder diffraction pattern of Form CS1 shows diffraction peaks at 2theta values of 16.8°±0.2°, 17.5°±0.2° and 22.2°±0.2°.

In a preferred embodiment, the X-ray powder diffraction pattern of Form CS1 shows characteristic peaks at 2theta values of 6.0°±0.2°, 6.7°±0.2°, 9.9°±0.2°, 14.2°±0.2°, 16.8°±0.2°, 17.5°±0.2°, 18.1°±0.2°, 20.3°±0.2° and 22.2°±0.2°.

Without any limitation being implied, in a specific example of the present disclosure, the X-ray powder diffraction pattern of Form CS1 is substantially as depicted in FIG. 1.

Without any limitation being implied, in a specific example of the present disclosure, Form CS1 is an anhydrate.

Without any limitation being implied, in a specific example of the present disclosure, when differential scanning calorimetry (DSC) is performed on Form CS1, an endothermic peak appears with onset temperature at around 90° C., and the DSC curve is substantially as depicted in FIG. 2.

Without any limitation being implied, in a specific example of the present disclosure, when thermo gravimetric analysis (TGA) is performed on Form CS1, the TGA curve shows about 1.6% weight loss when Form CS1 is heated to 113° C., and the TGA curve is substantially as depicted in FIG. 3.

According to the objective of the present disclosure, processes for preparing Form CS1 are also provided. The process comprises:

Method 1: dissolving NBI-98854 in an ester or mixture of an alkyl nitrile and an aromatic hydrocarbon, and evaporating at room temperature to obtain a solid, or Method 2: dissolving NBI-98854 in isopropanol or an alkyl nitrile, adding water to the obtained solution, stirring at certain temperature for a period of time, filtering and drying to obtain a solid. Said certain temperature is 0-35° C. Said a period of time is at least 1 day.

Furthermore, according to method 1, said ester is isopropyl acetate. Said alkyl nitrile is acetonitrile. Said aromatic hydrocarbon is toluene.

Furthermore, according to method 1, the volume ratio of the alkyl nitrile to the aromatic hydrocarbon is 1/10-10/1, more preferably 3/1.

Preferably, according to method 2, said alkyl nitrile is acetonitrile.

Preferably, according to method 2, said certain temperature is 0-30° C., more preferably 5° C.

Preferably, according to method 2, said a period of time is 2-10 days, more preferably 7 days.

According to the objective of the present disclosure, crystalline form CS2 of NBI-98854 is provided (hereinafter referred to as Form CS2).

Using CuKα radiation, the X-ray powder diffraction pattern of Form CS2 shows characteristic peaks at 2theta values of 7.4°±0.2°, 10.0°±0.2° and 18.4°±0.2°.

Furthermore, the X-ray powder diffraction pattern of Form CS2 shows 1 or 2 or 3 diffraction peaks at 2theta values of 4.6°±0.2°, 9.1°±0.2° and 14.2°±0.2°. Preferably, the X-ray powder diffraction pattern of Form CS2 shows diffraction peaks at 2theta values of 4.6°±0.2°, 9.1°±0.2° and 14.2°±0.2°.

Furthermore, the X-ray powder diffraction pattern of Form CS2 shows 1 or 2 or 3 diffraction peaks at 2theta values of 14.8°±0.2°, 17.2°±0.2° and 22.2°±0.2°. Preferably, the X-ray powder diffraction pattern of Form CS2 shows diffraction peaks at 2theta values of 14.8°±0.2°, 17.2°±0.2° and 22.2°±0.2°.

In a preferred embodiment, the X-ray powder diffraction pattern of Form CS2 shows characteristic peaks at 2theta values of 4.6°±0.2°, 7.4°±0.2°, 9.1°±0.2°, 10.0°±0.2°, 14.2°±0.2°、14.8°±0.2°, 17.2°±0.2°, 18.4°±0.2° and 22.2°±0.2°.

Without any limitation being implied, in a specific example of the present disclosure, the X-ray powder diffraction pattern of Form CS2 is substantially as depicted in FIG. 7.

Without any limitation being implied, in a specific example of the present disclosure, when DSC is performed on Form CS2, endothermic peak begins to appear at around 77° C., and the DSC curve is substantially as depicted in FIG. 8.

Without any limitation being implied, in a specific example of the present disclosure, when TGA is performed on Form CS2, the TGA curve shows about 3.7% weight loss gradient when Form CS2 is heated to 111° C., and the TGA curve is substantially as depicted in FIG. 9.

According to the objective of the present disclosure, a process for preparing Form CS2 is also provided. The process comprises:

Method 1: dissolving NBI-98854 in a mixture of a cyclic ether and water, and evaporating at room temperature to obtain a solid.

Method 2: dissolving NBI-98854 in a cyclic ether, and evaporating at room temperature to obtain a solid.

Method 3: dissolving NBI-98854 in methanol, adding water to the obtained solution, stirring at a certain temperature for a period of time, filtering and drying to obtain a solid. Said certain temperature is 0-35° C. Said a period of time is at least 1 day.

Preferably, according to method 1, said cyclic ether is tetrahydrofuran.

Preferably, according to method 1, the volume ratio of the cyclic ether to water is 1/10-10/1, more preferably 3/1.

Preferably, according to method 2, said cyclic ether is tetrahydrofuran.

Preferably, according to method 2, bioglass can be added during evaporation to induce precipitation.

Preferably, according to method 3, said certain temperature is 0-30° C., more preferably 5° C.

Preferably, according to method 3, said a period of time is 2-10 days, more preferably 7 days.

Another objective of the present disclosure is to provide a pharmaceutical composition comprising therapeutically effective amount of Form CS1, Form CS2 of NBI-98854 or combinations thereof and pharmaceutically acceptable excipients, which is generally prepared by mixing or combining therapeutically effective amount of Form CS1, Form CS2 of NBI-98854 or combinations thereof with one or more pharmaceutically acceptable excipients. The pharmaceutical compositions and formulations are prepared according to known methods in this field.

The present disclosure provides the use of Form CS1, Form CS2 of NBI-98854 or combinations thereof to prepare a drug product for preventing, delaying or treating tardive dyskinesia.

Another objective of the present disclosure is to provide the use of Form CS1, Form CS2 of NBI-98854 or combinations thereof or a pharmaceutical composition to prepare a drug product for treatment of tardive dyskinesia.

In the preparation processes of Form CS1 and Form CS2 of the present disclosure:

Said "room temperature" is not an accurate temperature value but refers to a temperature range of 10–30° C.

Said "evaporating" is accomplished by using a conventional method in the field such as slow evaporation and rapid evaporation. Slow evaporation is to seal the container with a sealing film and puncture holes for evaporation. Rapid evaporation is to place the container open for evaporation.

Said "stirring" is accomplished by using a conventional method in the field such as a magnetic stirring or a mechanical stirring and the stirring speed is 50-1800 r/min, preferably the magnetic stirring speed is 300-900 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished at room temperature or a higher temperature. The drying temperature is from room temperature to about 60° C., or to 40° C., or to 50° C. The drying time can be 2 to 48 hours, or overnight. Drying is accomplished in a fume hood, oven or vacuum oven.

The "bioglass" refers to a glass modified with silica.

The crystalline forms of NBI-98854 provided by the present disclosure have pharmaceutically acceptable solubility and hygroscopicity, good stability and are stable during storage, thereby avoiding changes in drug solubility, dissolution rate, bioavailability and efficacy due to polymorph transformation. Furthermore, the preparation processes of the crystalline forms CS1 and CS2 provided by the present disclosure are simple and reproducible. The crystallinity of the obtained crystal form is good. The morphologies of crystalline Form CS1 and Form CS2 are needle and block, respectively. Both forms disperse well and have little agglomeration, which are suitable for the development of drug product.

DETAILED DESCRIPTION OF THE PRESENT DISCLOSURE

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure. The abbreviations used in the present disclosure are explained as follows:

XRPD: X-ray Powder Diffraction
DSC: Differential Scanning calorimetry
TGA: Thermal Gravimetric Analysis
DVS: Dynamic Vapor Sorption
PLM: Polarized Light microscopy Instruments and methods used to collect data:

X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the differential scanning calorimetry (DSC) method of the present disclosure were as follows:

Heating rate: 10° C./min
Purge gas: nitrogen

Thermal gravimetric analysis (TGA) data in the present disclosure are acquired by a TA Q5000. The parameters of the thermal gravimetric analysis (TGA) method of the present disclosure were as follow:

Heating rate: 10° C./min
Purge gas: nitrogen

Dynamic Vapor Sorption (DVS) is measured via a SMS (Surface Measurement Systems Ltd.) intrinsic DVS. Its control software is DVS-Intrinsic control software, and its analysis software is DVS-Intrinsic analysis software. Typical Parameters for DVS test are as follows:

Temperature: 25° C.
Gas and flow rate: $N_2$, 200 mL/min
dm/dt: 0.002%/min
RH range: 0% RH to 95% RH High Performance Liquid Chromatography (HPLC) data in the present disclosure are collected from Agilent 1100 with diode array detector (DAD). The HPLC method parameters for purity test in the present disclosure are as follows:

1. Column: Waters Xbridge C18 150×4.6 mm, 5 μm
2. Mobile Phase: A: 0.1% TFA in $H_2O$
   B: 0.1% TFA in Acetonitrile
   Gradient:

| Time (min) | % B |
|---|---|
| 0.0 | 10 |
| 2.0 | 10 |
| 15.0 | 80 |
| 20.0 | 80 |
| 20.1 | 10 |
| 25.0 | 10 |

3. Flow rate: 1.0 mL/min
4. Injection Volume: 10 μL
5. Detection wavelength: 230 nm
6. Column Temperature: 40° C.
7. Diluent: 50% Acetonitrile Unless otherwise specified, the following examples were conducted at room temperature.

The solid of NBI-98854 used in the following examples can be obtained according to the method described in CN101553487B.

Example 1. Preparation of Form CS1

4.3 mg of NBI-98854 solid was charged into a 1.5-mL glass vial followed by dissolving into 0.5 mL of acetonitrile/toluene (3:1, v/v) solvent mixture to obtain a clear solution. Solid was obtained by slow evaporation at RT.

Figure 1:
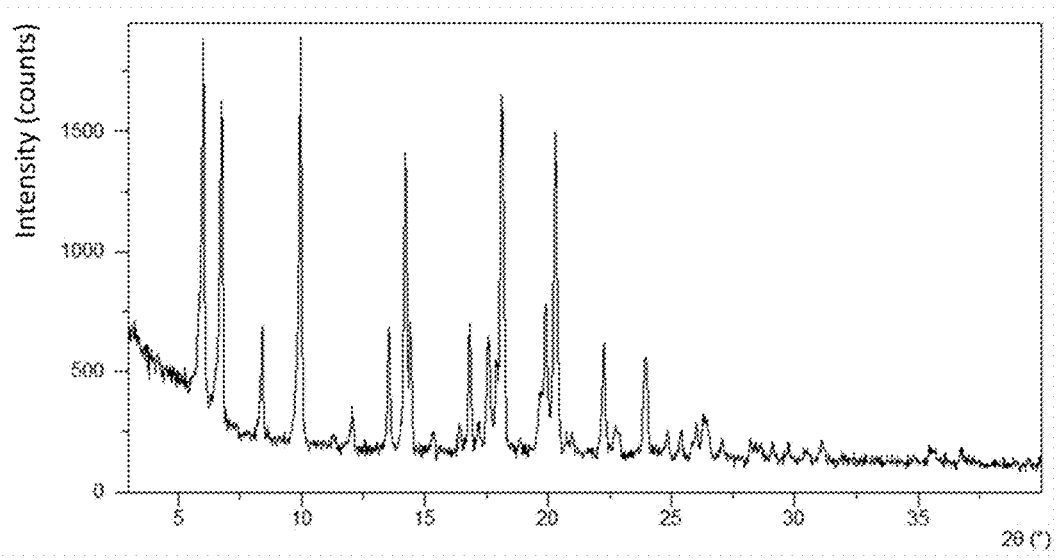
FIG. 1 shows an XRPD pattern of Form CS1 in example 1.
Figure 2:
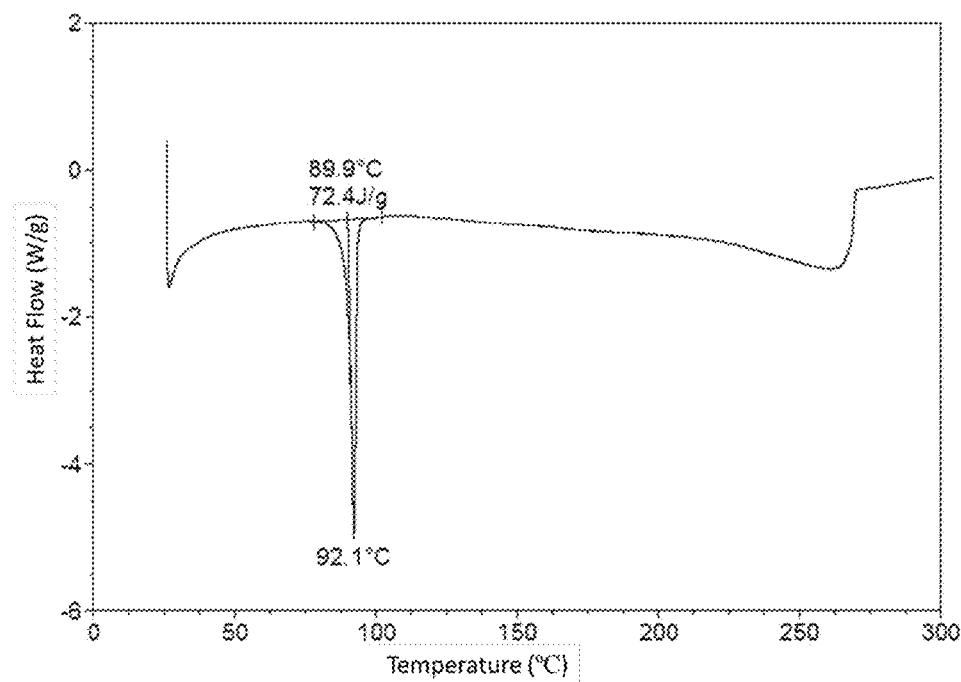
FIG. 2 shows a DSC curve of Form CS1 in example 1.
Figure 3:
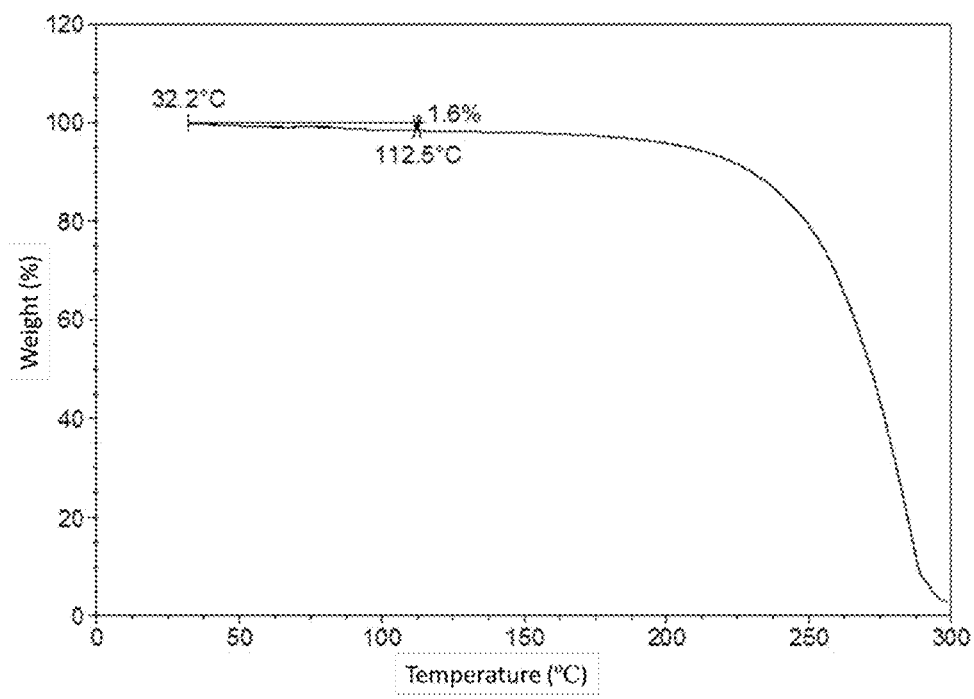
FIG. 3 shows a TGA curve of Form CS1 in example 1.

The obtained solid in this example was confirmed to be Form CS1. The X-ray powder diffraction data of the obtained solid is shown in Table 1, while the XRPD pattern is substantially as depicted in FIG. 1, the DSC curve is substantially as depicted in FIG. 2, and the TGA curve is substantially as depicted in FIG. 3.

TABLE 1

| 2θ | d spacing | Intensity % |
|---|---|---|
| 6.00 | 14.74 | 94.30 |
| 6.74 | 13.11 | 76.17 |
| 8.37 | 10.56 | 27.55 |
| 9.94 | 8.90 | 100.00 |
| 12.03 | 7.36 | 8.26 |
| 13.52 | 6.55 | 30.81 |
| 14.21 | 6.23 | 73.04 |
| 14.41 | 6.15 | 29.48 |
| 15.30 | 5.79 | 4.25 |
| 16.40 | 5.41 | 6.89 |
| 16.81 | 5.27 | 31.44 |
| 17.16 | 5.17 | 6.92 |
| 17.55 | 5.05 | 28.19 |
| 18.10 | 4.90 | 91.19 |
| 19.88 | 4.47 | 37.92 |
| 20.28 | 4.38 | 80.56 |
| 22.23 | 4.00 | 28.09 |
| 22.77 | 3.91 | 6.29 |
| 23.93 | 3.72 | 25.12 |
| 24.81 | 3.59 | 5.60 |
| 25.37 | 3.51 | 6.18 |
| 26.00 | 3.43 | 8.96 |
| 26.35 | 3.38 | 9.50 |
| 27.03 | 3.30 | 3.85 |
| 28.18 | 3.17 | 4.57 |
| 29.09 | 3.07 | 4.04 |
| 31.10 | 2.88 | 4.58 |
| 35.64 | 2.52 | 2.50 |
| 36.70 | 2.45 | 3.35 |

Example 2. Preparation of Form CS1

4.5 mg of NBI-98854 solid was charged into a 1.5-mL glass vial followed by dissolving into 0.5 mL of isopropyl acetate to obtain a clear solution. Solid was obtained by slow evaporation at RT.

Figure 4:
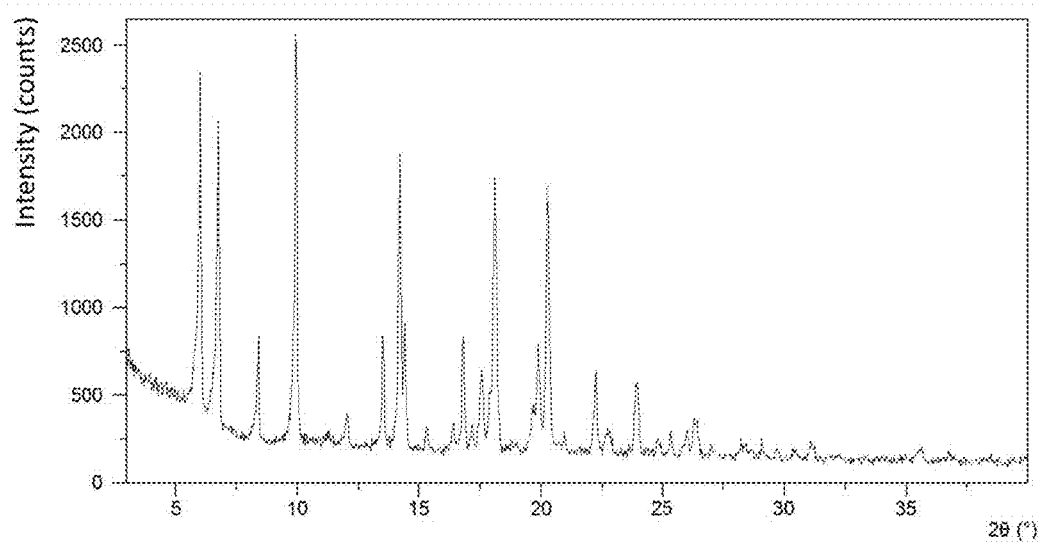
FIG. 4 shows an XRPD pattern of Form CS1 in example 2.

The obtained solid in this example was confirmed to be Form CS1. The X-ray powder diffraction data of the obtained solid is shown in Table 2, while the XRPD pattern is substantially as depicted in FIG. 4.

TABLE 2

| 2θ | d spacing | Intensity % |
|---|---|---|
| 6.00 | 14.73 | 87.47 |
| 6.74 | 13.11 | 73.27 |
| 8.38 | 10.55 | 25.58 |
| 9.94 | 8.90 | 100.00 |
| 12.02 | 7.37 | 7.78 |
| 13.51 | 6.55 | 29.33 |
| 14.21 | 6.23 | 70.36 |
| 14.42 | 6.14 | 30.73 |
| 15.31 | 5.79 | 5.65 |
| 16.40 | 5.41 | 6.87 |
| 16.81 | 5.27 | 28.36 |
| 17.17 | 5.16 | 6.82 |
| 17.56 | 5.05 | 20.28 |
| 18.10 | 4.90 | 69.43 |
| 19.88 | 4.47 | 26.84 |
| 20.27 | 4.38 | 65.85 |
| 20.97 | 4.24 | 4.40 |
| 22.24 | 4.00 | 21.03 |
| 22.72 | 3.91 | 5.66 |
| 23.90 | 3.72 | 17.19 |
| 24.81 | 3.59 | 3.53 |
| 25.34 | 3.51 | 5.35 |
| 26.01 | 3.43 | 6.23 |
| 26.34 | 3.38 | 8.39 |
| 27.06 | 3.29 | 1.83 |
| 28.28 | 3.16 | 3.08 |
| 29.07 | 3.07 | 3.59 |
| 29.67 | 3.01 | 2.19 |
| 30.44 | 2.94 | 1.85 |
| 31.10 | 2.88 | 4.11 |
| 35.57 | 2.52 | 2.79 |
| 36.86 | 2.44 | 1.17 |

Example 3. Preparation of Form CS1

8.4 mg of NBI-98854 solid was charged into a 1.5-mL glass vial followed by dissolving into 30 μL of acetonitrile to obtain a clear solution. 0.3 mL of water was added under magnetic stirring. The obtained solution was stirred at 5° C. for 7 days, then filtered and dried to obtain a solid.

Figure 5:
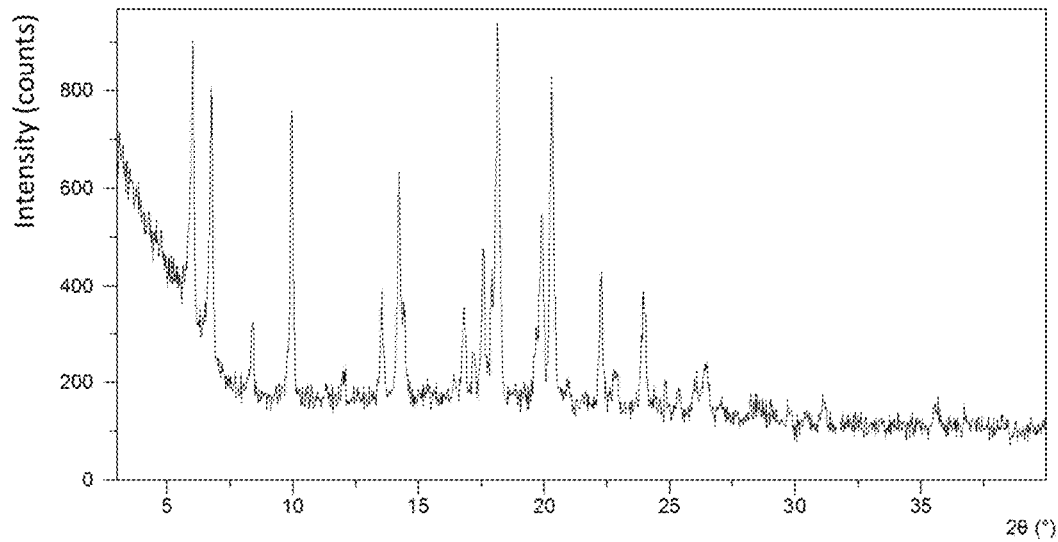
FIG. 5 shows an XRPD pattern of Form CS1 in example 3.

The obtained solid in this example was confirmed to be Form CS1. The X-ray powder diffraction data of the obtained solid is shown in Table 3, while the XRPD pattern is substantially as depicted in FIG. 5.

TABLE 3

| 2θ | d spacing | Intensity % |
|---|---|---|
| 5.99 | 14.75 | 69.88 |
| 6.73 | 13.13 | 67.24 |
| 8.38 | 10.55 | 18.15 |
| 9.93 | 8.91 | 74.89 |
| 11.98 | 7.38 | 6.50 |
| 13.49 | 6.56 | 30.17 |
| 14.20 | 6.24 | 59.88 |
| 16.79 | 5.28 | 26.15 |
| 17.17 | 5.16 | 14.93 |
| 17.55 | 5.05 | 42.03 |
| 18.14 | 4.89 | 100.00 |
| 19.89 | 4.46 | 51.03 |
| 20.27 | 4.38 | 82.10 |
| 20.94 | 4.24 | 8.32 |
| 22.23 | 4.00 | 35.13 |
| 22.82 | 3.90 | 10.90 |
| 23.98 | 3.71 | 27.67 |
| 24.80 | 3.59 | 8.91 |
| 25.32 | 3.52 | 6.90 |
| 26.01 | 3.43 | 9.66 |
| 26.45 | 3.37 | 14.10 |
| 28.34 | 3.15 | 4.06 |
| 29.74 | 3.00 | 3.82 |
| 30.40 | 2.94 | 2.68 |
| 31.11 | 2.87 | 6.21 |
| 35.58 | 2.52 | 4.51 |

Example 4. Preparation of Form CS1

8.5 mg of NBI-98854 solid was charged into a 1.5-mL glass vial followed by dissolving into 50 μL of isopropanol to obtain a clear solution. 0.3 mL water was added under magnetic stirring. The obtained solution was stirred at 5° C. for 7 days, then filtered and dried to obtain a solid.

Figure 6:
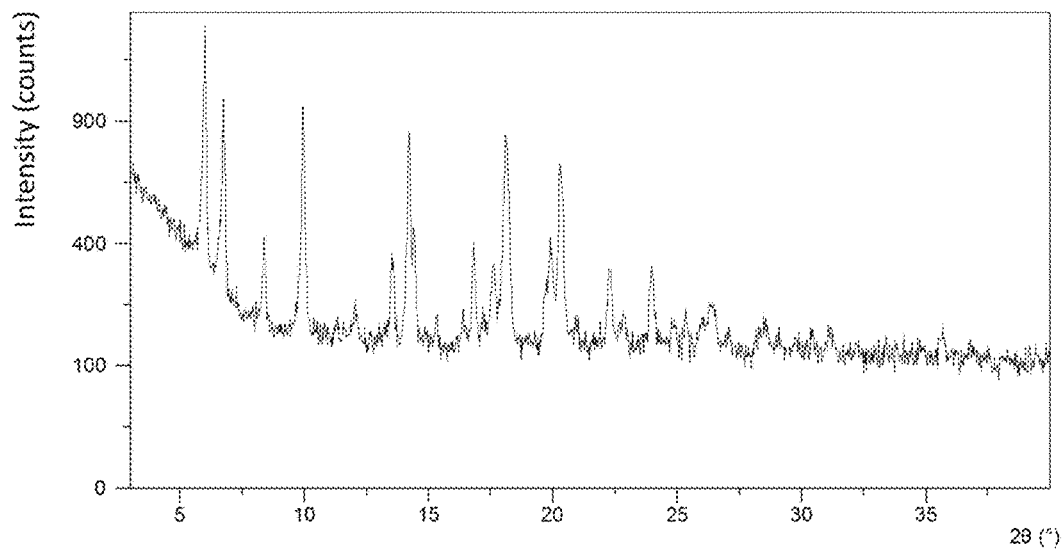
FIG. 6 shows an XRPD pattern of Form CS1 in example 4.

The obtained solid in this example was confirmed to be Form CS1. The X-ray powder diffraction data of the obtained solid is shown in Table 4, while the XRPD pattern is substantially as depicted in FIG. 6.

TABLE 4

| 2θ | d spacing | Intensity % |
|---|---|---|
| 6.00 | 14.73 | 100.00 |
| 6.75 | 13.09 | 69.68 |
| 8.39 | 10.54 | 19.54 |
| 9.95 | 8.89 | 73.36 |
| 11.33 | 7.81 | 4.14 |
| 12.04 | 7.35 | 6.39 |
| 13.54 | 6.54 | 17.11 |
| 14.22 | 6.23 | 65.68 |
| 14.43 | 6.14 | 27.75 |
| 16.40 | 5.41 | 5.75 |
| 16.83 | 5.27 | 24.37 |
| 17.60 | 5.04 | 19.42 |
| 18.09 | 4.90 | 67.12 |
| 19.91 | 4.46 | 24.64 |
| 20.27 | 4.38 | 51.73 |
| 22.27 | 3.99 | 18.34 |
| 22.88 | 3.89 | 6.97 |
| 23.94 | 3.72 | 19.30 |
| 24.84 | 3.58 | 4.88 |
| 25.34 | 3.51 | 6.40 |
| 26.36 | 3.38 | 9.68 |

Example 5. Preparation of Form CS2

4.5 mg of NBI-98854 solid was charged into a 1.5-mL glass vial followed by dissolving into 0.5 mL of tetrahydrofuran to obtain a clear solution. 0.2 mg of bioglass was added subsequently. Solid was obtained by slow evaporation at RT.

Figure 7:
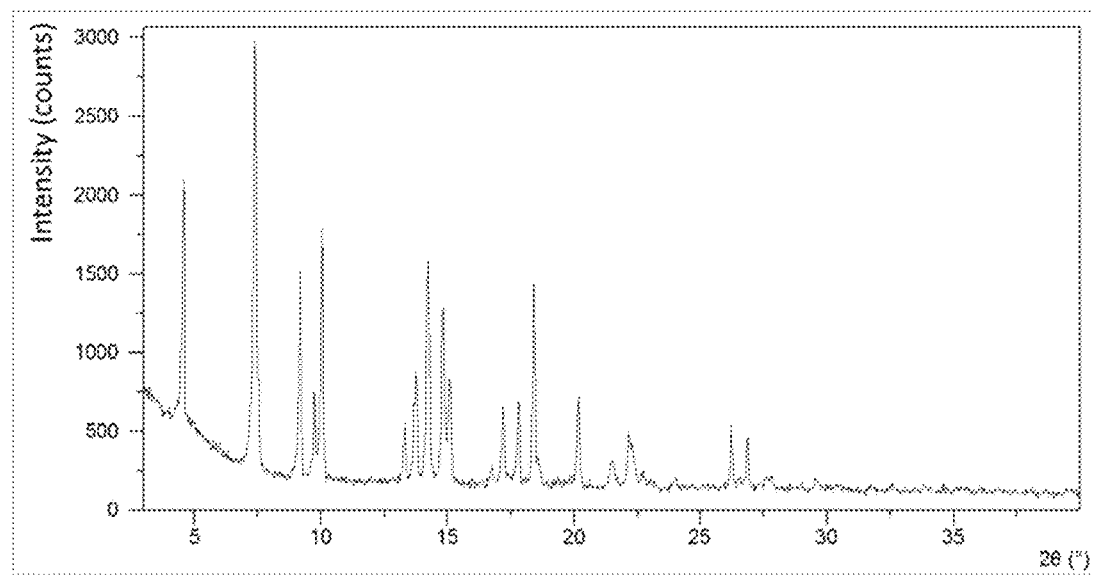
FIG. 7 shows an XRPD pattern of Form CS2 in example 5.
Figure 8:
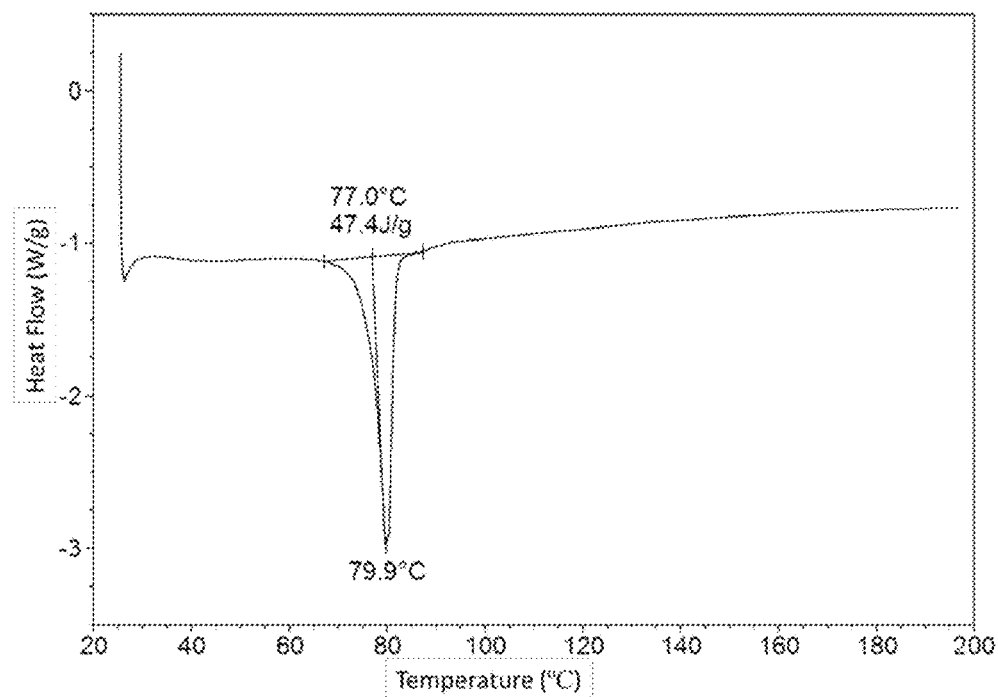
FIG. 8 shows a DSC curve of Form CS2 in example 5.
Figure 9:
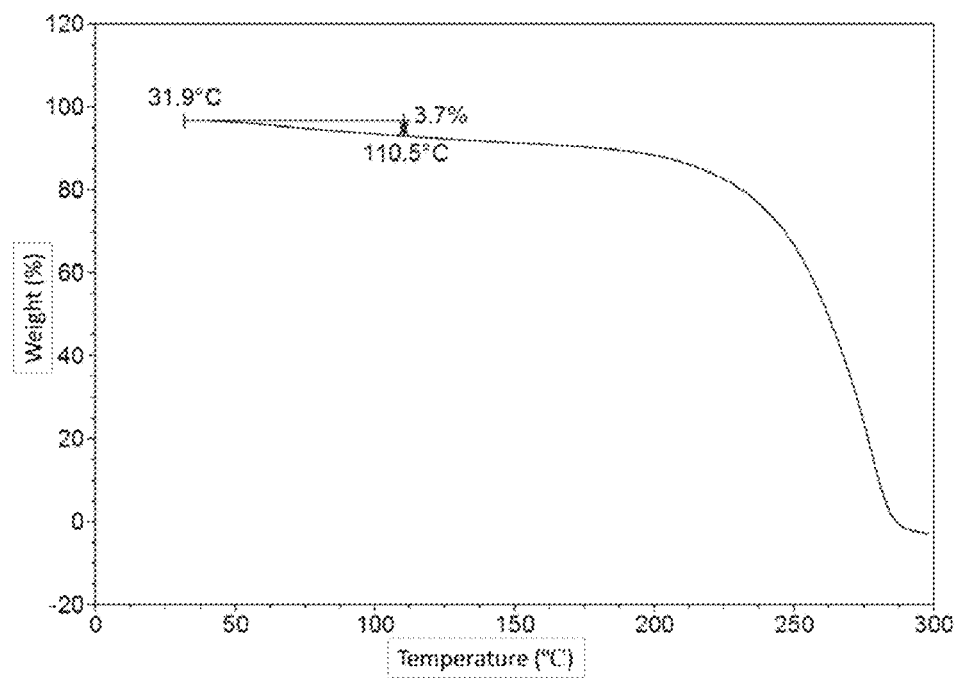
FIG. 9 shows a TGA curve of Form CS2 in example 5.

The obtained solid in this example was confirmed to be Form CS2. The X-ray powder diffraction data of the obtained solid is shown in Table 5, while the XRPD pattern is substantially as depicted in FIG. 7, the DSC curve is substantially as depicted in FIG. 8, and the TGA curve is substantially as depicted in FIG. 9.

TABLE 5

| 2θ | d spacing | Intensity % |
|---|---|---|
| 4.56 | 19.39 | 56.67 |
| 7.37 | 11.99 | 100.00 |
| 9.15 | 9.67 | 44.79 |
| 9.71 | 9.11 | 20.18 |
| 10.02 | 8.83 | 56.22 |
| 13.30 | 6.65 | 13.62 |
| 13.76 | 6.44 | 25.72 |
| 14.22 | 6.23 | 51.43 |
| 14.81 | 5.98 | 40.78 |
| 15.08 | 5.88 | 24.42 |
| 16.74 | 5.30 | 4.41 |
| 17.18 | 5.16 | 18.01 |
| 17.79 | 4.99 | 18.41 |
| 18.39 | 4.82 | 46.48 |
| 20.15 | 4.41 | 19.35 |
| 21.49 | 4.14 | 5.72 |
| 22.13 | 4.02 | 12.08 |
| 23.98 | 3.71 | 1.81 |
| 26.20 | 3.40 | 14.38 |
| 26.84 | 3.32 | 10.81 |
| 27.78 | 3.21 | 2.99 |
| 29.55 | 3.02 | 2.46 |

Example 6. Preparation of Form CS2

4.5 mg of NBI-98854 solid was charged into a 1.5-mL glass vial followed by dissolving into 0.5 mL of tetrahydrofuran/water (3:1, v/v) solvent mixture to obtain a clear solution. Solid was obtained by slow evaporation at RT.

Figure 10:
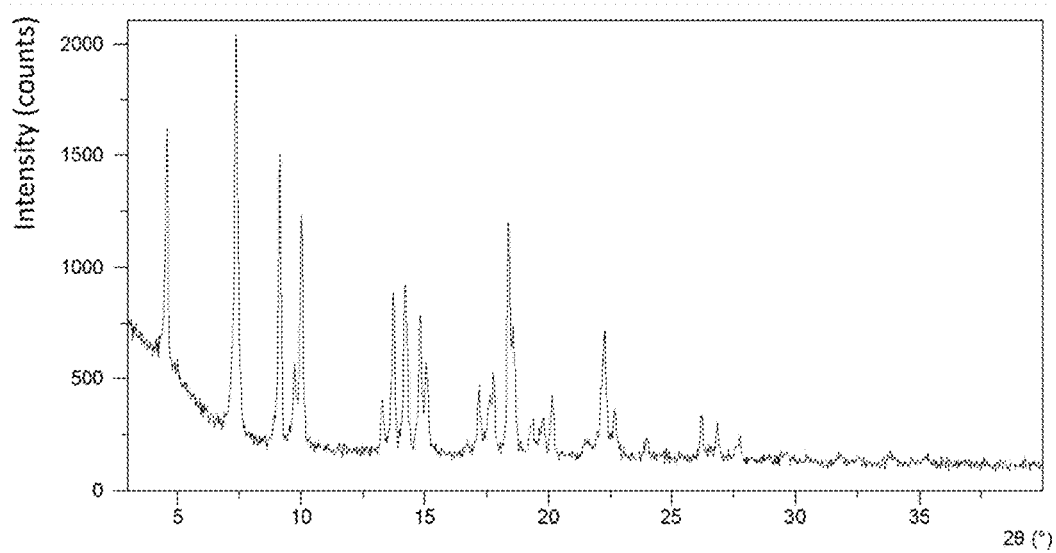
FIG. 10 shows an XRPD pattern of Form CS2 in example 6.

The obtained solid in this example was confirmed to be Form CS2. The X-ray powder diffraction data of the obtained solid is shown in Table 6, while the XRPD pattern is substantially as depicted in FIG. 10.

TABLE 6

| 2θ | d spacing | Intensity % |
|---|---|---|
| 4.58 | 19.29 | 59.45 |
| 7.37 | 11.99 | 100.00 |
| 9.14 | 9.68 | 73.31 |
| 9.72 | 9.10 | 21.72 |
| 10.01 | 8.83 | 58.75 |
| 13.30 | 6.66 | 13.21 |
| 13.74 | 6.44 | 41.62 |
| 14.22 | 6.23 | 43.81 |
| 14.82 | 5.98 | 35.04 |
| 15.08 | 5.87 | 22.54 |
| 17.18 | 5.16 | 16.90 |
| 17.78 | 4.99 | 20.48 |
| 18.38 | 4.83 | 62.46 |
| 18.60 | 4.77 | 28.56 |
| 19.36 | 4.58 | 9.13 |
| 19.76 | 4.49 | 9.22 |
| 20.15 | 4.41 | 14.32 |
| 22.27 | 3.99 | 32.18 |
| 22.66 | 3.92 | 11.80 |
| 23.93 | 3.72 | 4.92 |
| 26.22 | 3.40 | 9.94 |
| 26.82 | 3.32 | 9.82 |
| 27.74 | 3.22 | 5.71 |
| 31.75 | 2.82 | 2.31 |
| 33.86 | 2.65 | 2.09 |

Example 7. Preparation of Form CS2

7.8 mg of NBI-98854 solid was charged into a 1.5-mL glass vial followed by dissolving in 30 μL of methanol to obtain a clear solution. 0.3 mL of water was added under magnetic. The obtained solution was stirred at 5° C. for 7 days, then filtered and dried to obtain a solid.

Figure 11:
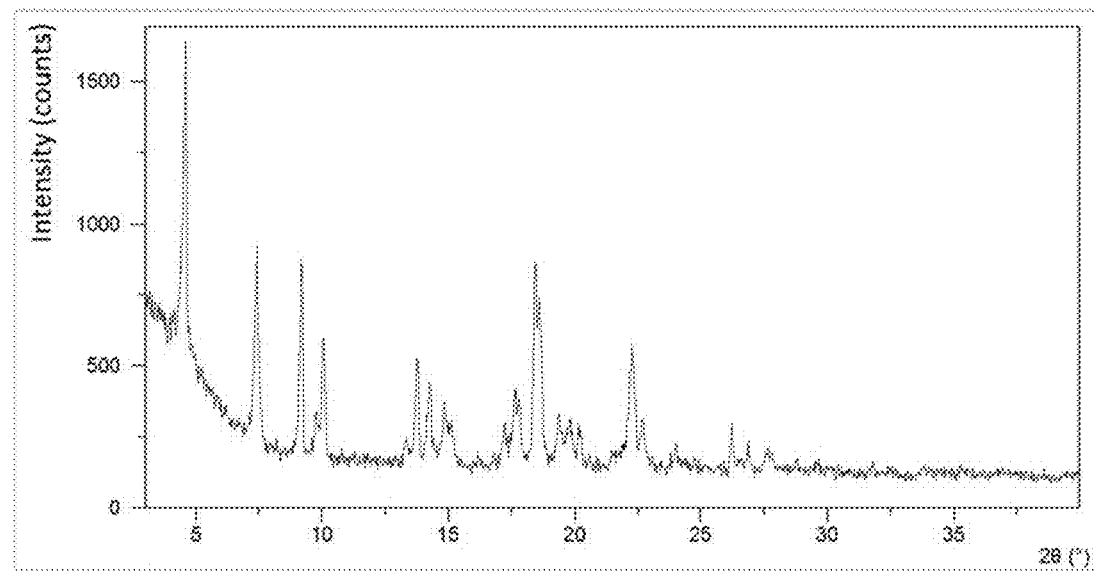
FIG. 11 shows an XRPD pattern of Form CS2 in example 7.

The obtained solid in this example was confirmed to be Form CS2. The X-ray powder diffraction data of the obtained solid is shown in Table 7, while the XRPD pattern is substantially as depicted in FIG. 11.

TABLE 7

| 2θ | d spacing | Intensity % |
|---|---|---|
| 4.55 | 19.41 | 100.00 |
| 7.37 | 11.99 | 56.74 |
| 9.14 | 9.68 | 58.34 |
| 10.01 | 8.83 | 36.49 |
| 13.27 | 6.67 | 6.74 |
| 13.75 | 6.44 | 33.22 |
| 14.23 | 6.23 | 25.12 |
| 14.79 | 5.99 | 19.19 |
| 17.17 | 5.17 | 11.39 |
| 17.60 | 5.04 | 23.13 |
| 18.38 | 4.83 | 62.21 |
| 18.58 | 4.77 | 47.35 |
| 19.33 | 4.59 | 16.57 |
| 19.78 | 4.49 | 14.27 |
| 20.12 | 4.41 | 11.93 |
| 22.24 | 4.00 | 37.86 |
| 22.61 | 3.93 | 15.50 |
| 23.97 | 3.71 | 6.49 |
| 26.18 | 3.40 | 14.11 |
| 26.85 | 3.32 | 6.57 |
| 27.63 | 3.23 | 5.06 |

Example 8. Hygroscopicity Experiment of Form CS1

Figure 12:
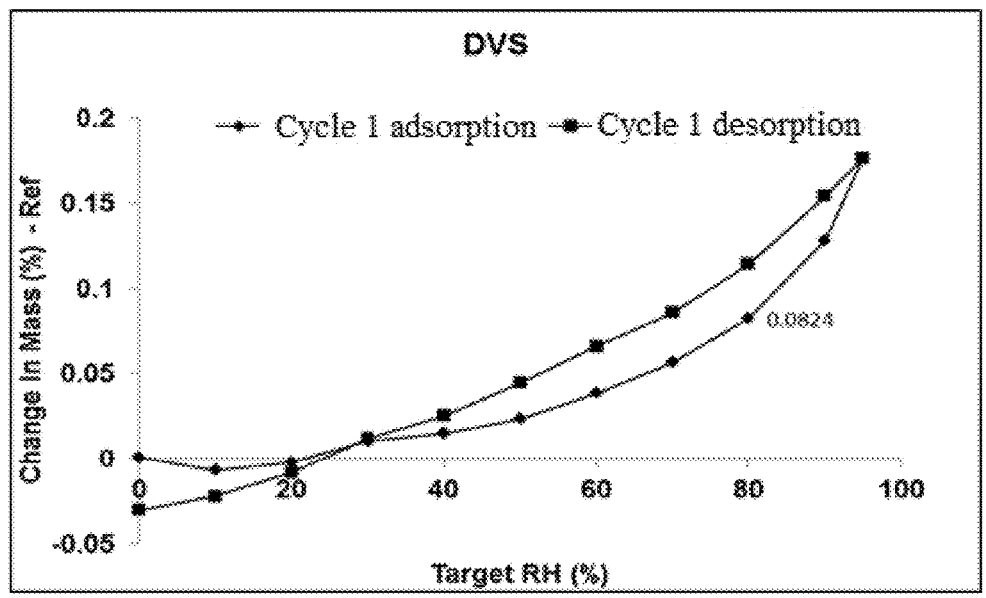
FIG. 12 shows a DVS plot of Form CS1 in example 8.

14.3 mg of Form CS1 was placed in a DVS instrument and underwent a cycle of 0%-95%-0% RH. The DVS curve is substantially as depicted in FIG. 12. A weight gain of 0.08% is observed at 80% RH. Form CS1 is almost non hygroscopic.

Example 9. Hygroscopicity Experiment of Form CS2

Figure 13:
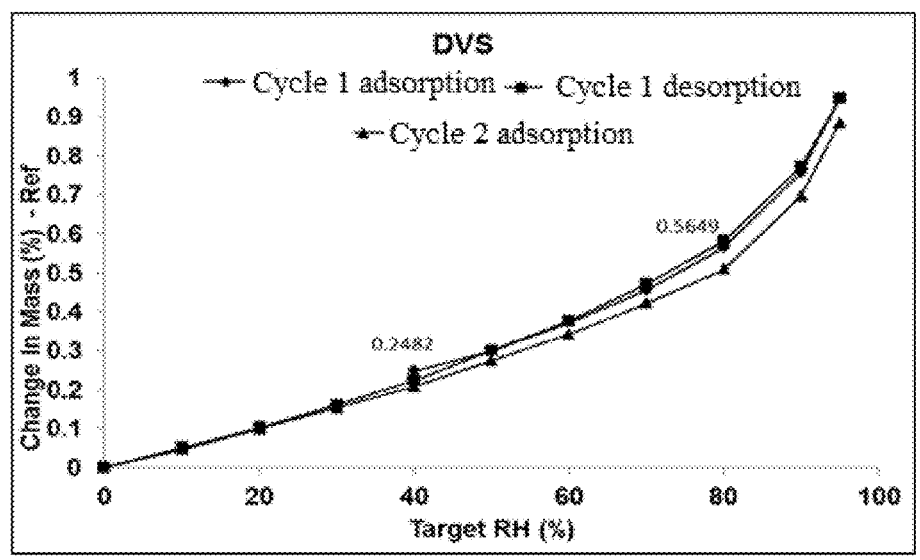
FIG. 13 shows a DVS plot of Form CS2 in example 9.

8.6 mg of Form CS2 was placed in a DVS instrument and underwent a cycle of 40%-95%-0%-95% RH. The DVS curve is shown in FIG. 13. A weight gain of 0.56% is observed at 80% RH. Form CS2 is slightly hygroscopic and has advantages during storage and transportation of the drug products.

Description and definition of hygroscopicity (Chinese Pharmacopoeia 2015 edition appendix Drug hygroscopic test guidelines, test at 25° C.+/−1° C., 80% RH):

Deliquescent: Sufficient water is absorbed to form a liquid;
Very hygroscopic: Increase in mass is equal to or greater than 15 percent;
Hygroscopic: Increase in mass is less than 15 percent and equal to or greater than 2 percent;
Slightly hygroscopic: Increase in mass is less than 2 percent and equal to or greater than 0.2 percent;
Non hygroscopic or almost non hygroscopic: Increase in mass is less than 0.2%.

Example 10. Stability Assessment of Form CS1

Figure 14:
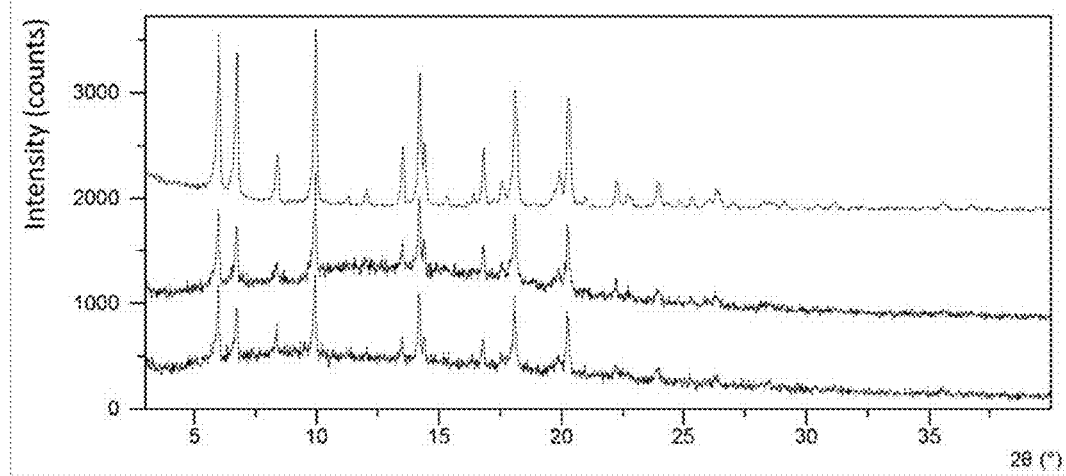
FIG. 14 shows the XRPD pattern overlay of Form CS1 before and after stability test in example 10 (Above is the initial sample, in the middle is the sample placed under 25° C./60% RH for 1 month, the bottom is the sample placed under 40° C./75% RH for 1 month).

Form CS1 in the present disclosure was stored under different conditions of 25° C./60% RH and 40° C./75% RH for 1 month. Samples were taken at the end of 1 month. XRPD and HPLC were used to test the crystalline form and chemical purity. The experimental results are summarized in Table 8. The XRPD overlay is shown in FIG. 14 (Above is the initial sample, in the middle is the sample placed under 25° C./60% RH for 1 month, at the bottom is the sample placed under 40° C./75% RH for 1 month).

TABLE 8

| Initial sample | Initial purity | Conditions | Purity | Crystalline form |
|---|---|---|---|---|
| Form CS1 | 98.02% | 25° C./60% RH (1 month) | 98.21% | unchanged |
| Form CS1 | | 40° C./75%RH (1 month) | 97.76% | unchanged |

The results show that Form CS1 has no form change and no significant purity change after placing under 25° C./60% RH and 40° C./75% RH for 1 month. It can be seen that Form CS1 has good stability.

Example 11. Stability Experiment of Form CS2

Figure 15:
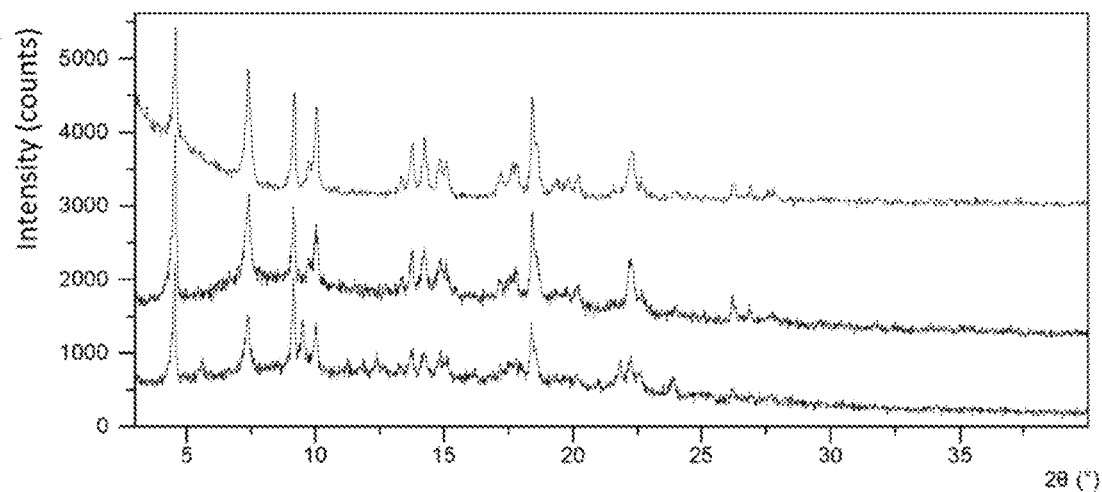
FIG. 15 shows the XRPD pattern overlay of Form CS2 before and after stability test in example 11 (Above is the initial sample, in the middle is the sample placed under 25° C./60% RH for 1 month, at the bottom is the sample placed under 40° C./75% RH for 1 month).

Form CS2 in the present disclosure was stored under different conditions of 25° C./60% RH and 40° C./75% RH for 1 month. Samples were taken at the end of 1 month. XRPD and HPLC were used to test the crystalline form and chemical purity. The experimental results are summarized in Table 9. the XRPD overlay is shown in FIG. 15 (Above is the initial sample, in the middle is the sample placed under 25° C./60% RH for 1 month, at the bottom is the sample placed under 40° C./75% RH for 1 month).

TABLE 9

| Initial sample | Initial purity | Conditions | Purity | Crystalline form |
|---|---|---|---|---|
| Form CS2 | 98.34% | 25° C./60% RH (1 month) | 98.60% | unchanged |
| Form CS2 | | 40° C./75% RH (1 month) | 97.38% | unchanged |

The results show that Form CS2 has no form change and no significant purity change after placing under 25° C./60% RH and 40° C./75% RH for 1 month. It can be seen that Form CS2 has a good stability.

Example 12. The Morphology Test of Form CS1 and Form CS2

Figure 16:
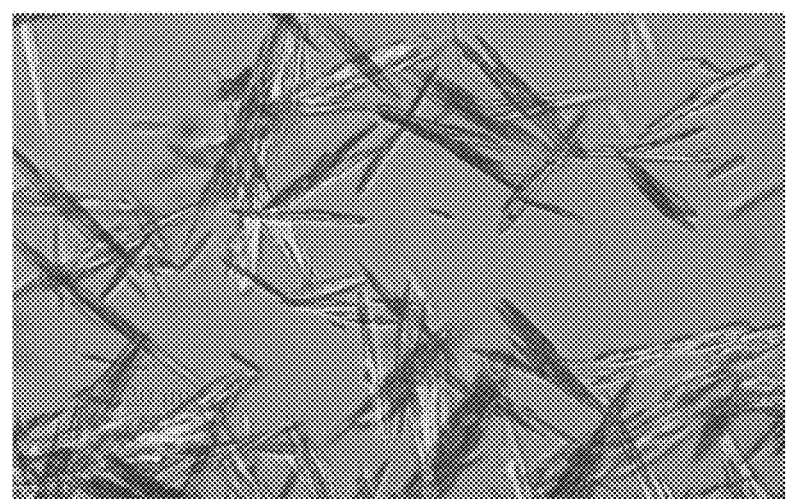
FIG. 16 shows a PLM image of Form CS1 in example 12.
Figure 17:
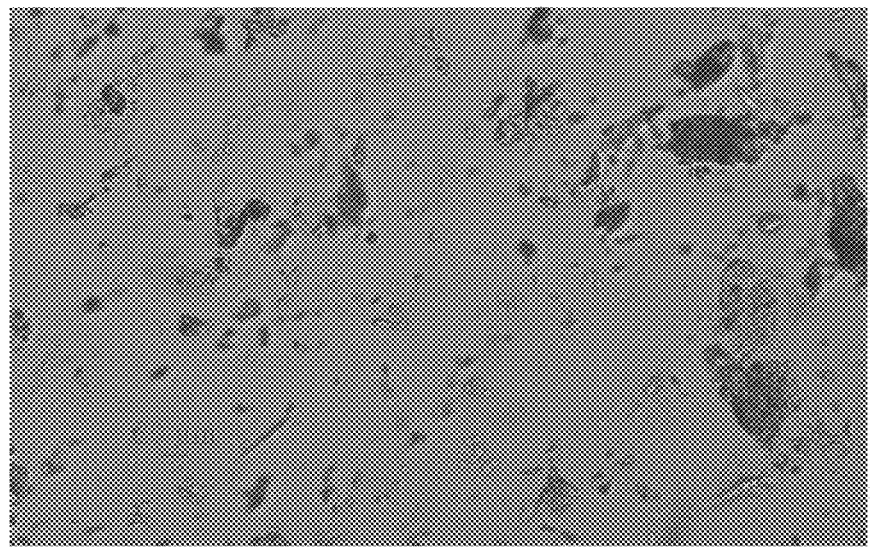
FIG. 17 shows a PLM image of Form CS2 in example 12.

Form CS1 and Form CS2 in the present disclosure were tested by polarized light microscopy, and the results were depicted in FIG. 16 and FIG. 17. The morphologies of Form CS1 and Form CS2 are needle and block, respectively. Both forms disperse well and have little agglomeration. It can be seen from the PLM images that the morphologies of Form CS1 and Form CS2 in the present disclosure are suitable for the development of drug product.

Those skilled in the art will understand that, under the teachings of this specification, it can make some modifications or variations of the present disclosure. Such modifications and variations are also in the scope of claims defined in the present disclosure.

What is claimed is:

1. A crystalline form CS1 of NBI-98854, wherein the X-ray powder diffraction pattern shows characteristic peaks at 2theta values of 9.9°±0.2°, 18.1°±0.2° and 20.3°±0.2° using CuKα radiation.

2. The crystalline form CS1 according to claim 1, wherein the X-ray powder diffraction pattern shows 1 or 2 or 3 characteristic peaks at 2theta values of 6.0°±0.2°, 6.7°±0.2° and 14.2°±0.2°.

3. The crystalline form CS1 according to claim 1, wherein the X-ray powder diffraction pattern shows 1 or 2 or 3 characteristic peaks at 2theta values of 16.8°±0.2°, 17.5°±0.2° and 22.2°±0.2°.

4. A process for preparing crystalline form CS1 according to claim 1, wherein the process comprises:
1) dissolving NBI-98854 in an ester or mixture of an alkyl nitrile and an aromatic hydrocarbon, and evaporating at room temperature to obtain a solid, or
2) dissolving NBI-98854 in isopropanol or an alkyl nitrile, adding water to the obtained solution, stirring at certain temperature for a period of time, filtering and drying to obtain a solid, wherein said certain temperature is 0-35° C., said period of time is at least 1 day.

5. The process for preparing crystalline form CS1 according to claim 4, wherein in the step 1), said alkyl nitrile is acetonitrile, said aromatic hydrocarbon is toluene, and the volume ratio of the alkyl nitrile to the aromatic hydrocarbon is from 1/10-10/1; in the step 2), said alkyl nitrile is acetonitrile, said certain temperature is 0-30° C., and said period of time is 2-10 days.

6. A crystalline form CS2 of NBI-98854, wherein the X-ray powder diffraction pattern shows characteristic peaks at 2theta values of 7.4°±0.2°, 10.0°±0.2° and 18.4°±0.2° using CuKα radiation.

7. The crystalline form CS2 according to claim 6, wherein the X-ray powder diffraction pattern shows 1 or 2 or 3 characteristic peaks at 2theta values of 4.6°±0.2°, 9.1°±0.2° and 14.2°±0.2°.

8. The crystalline form CS2 according to claim 6, wherein the X-ray powder diffraction pattern shows 1 or 2 or 3 characteristic peaks at 2theta values of 14.8°±0.2°, 17.2°±0.2° and 22.2°±0.2°.

9. A process for preparing crystalline form CS2 according to claim 6, wherein the process comprises:
   1) dissolving NBI-98854 in a mixture of a cyclic ether and water, and evaporating at room temperature to obtain a solid, or
   2) dissolving NBI-98854 in a cyclic ether, and evaporating at room temperature to obtain a solid, or
   3) dissolving NBI-98854 in methanol, adding water to the obtained solution, stirring at certain temperature for a period of time, filtering and drying to obtain a solid, wherein said certain temperature is 0-35° C., said period of time is at least 1 day.

10. The process for preparing crystalline form CS2 according to claim 9, wherein in the step 1), said cyclic ether is tetrahydrofuran, the volume ratio of the cyclic ether to water is 1/10-10/1; in the step 2), said cyclic ether is tetrahydrofuran; in the step 3), said certain temperature is 0-30° C., and said period of time is 2-10 days.

11. A pharmaceutical composition, wherein said pharmaceutical composition comprises a therapeutically effective amount of the crystalline form CS1 of NBI-98854 according to claim 1, and pharmaceutically acceptable carriers, diluents or excipients.

12. A method of treating tardive dyskinesia, comprising administering to a patient in need thereof a therapeutically effective amount of the crystalline form CS1 of NBI-98854 according to claim 1.

13. A pharmaceutical composition, wherein said pharmaceutical composition comprises a therapeutically effective amount of the crystalline form CS2 of NBI-98854 according to claim 6, and pharmaceutically acceptable carriers, diluents or excipients.

14. A method of treating tardive dyskinesia, comprising administering to a patient in need thereof a therapeutically effective amount of the crystalline form CS2 of NBI-98854 according to claim 6.

* * * * *